(12) United States Patent
Bush et al.

(10) Patent No.: US 12,241,877 B2
(45) Date of Patent: Mar. 4, 2025

(54) ANALYTICAL METHOD

(71) Applicant: R.P. Scherer Technologies, LLC, Carson City, NV (US)

(72) Inventors: William Derek Bush, Belleair, FL (US); Ryan Scott Cormier, Palm Harbor, FL (US); Karunakar Sukuru, St. Petersburg, FL (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 517 days.

(21) Appl. No.: 17/594,195

(22) PCT Filed: Apr. 7, 2020

(86) PCT No.: PCT/US2020/026990
§ 371 (c)(1),
(2) Date: Oct. 6, 2021

(87) PCT Pub. No.: WO2020/210185
PCT Pub. Date: Oct. 15, 2020

(65) Prior Publication Data
US 2022/0178886 A1 Jun. 9, 2022

Related U.S. Application Data

(60) Provisional application No. 62/831,104, filed on Apr. 8, 2019.

(51) Int. Cl.
*G01N 30/14* (2006.01)
*A61K 9/48* (2006.01)
*G01N 30/02* (2006.01)

(52) U.S. Cl.
CPC .............. *G01N 30/14* (2013.01); *A61K 9/48* (2013.01); *G01N 2030/027* (2013.01)

(58) Field of Classification Search
None
See application file for complete search history.

(56) References Cited

U.S. PATENT DOCUMENTS 6,187,595 B1 * 2/2001 Staal .................... G01N 21/82
250/576
6,984,404 B1 1/2006 Talton
(Continued)

FOREIGN PATENT DOCUMENTS

JP 2003516926 A 5/2003
JP 2015510899 A 4/2015
(Continued)

OTHER PUBLICATIONS

Datasheets for Sodium Caprate, HPMC and GLP-1 including molecular weights. Retrieved Apr. 15, 2024 (Year: 2024).*
(Continued)

*Primary Examiner* — Patrick Assouad
*Assistant Examiner* — Mark A Shabman
(74) *Attorney, Agent, or Firm* — Lowenstein Sandler LLP

(57) ABSTRACT

Disclosed herein are methods, systems, and kits for determining the total amount of a coating polymer in a dosage form. The coating polymer may be a polydisperse polymer having a plurality of molecular weights. The instant disclosure enables to accurately, reliably, and efficiently determine the total amount of a polydisperse polymer in a dosage form that includes one or more other constituents that have a molecular weight range that overlap with at least some of the polydisperse polymer's molecular weight.

12 Claims, 4 Drawing Sheets

(56) References Cited

U.S. PATENT DOCUMENTS

| | | | |
|---|---|---|---|
| 2010/0148070 A1 | 6/2010 | Ho | |
| 2010/0203130 A1* | 8/2010 | Tygesen | A61K 31/4458 73/866 |
| 2010/0239667 A1* | 9/2010 | Hemmingsen | A61K 31/167 424/495 |
| 2015/0099003 A1 | 4/2015 | Song et al. | |
| 2015/0276690 A1 | 10/2015 | Hudalla et al. | |
| 2015/0335753 A1* | 11/2015 | Desai | A61K 9/4866 424/490 |
| 2015/0368407 A1* | 12/2015 | Zhang | B01J 13/14 521/149 |
| 2018/0015112 A1* | 1/2018 | Tabuteau | A61K 9/2004 |
| 2018/0263915 A1* | 9/2018 | Nybo | A61K 9/5047 |
| 2018/0340174 A1* | 11/2018 | Lundorf | C12N 15/1065 |

FOREIGN PATENT DOCUMENTS

| | | |
|---|---|---|
| WO | 00028969 A2 | 5/2000 |
| WO | 2011024049 A2 | 3/2011 |

OTHER PUBLICATIONS

Katori Noriko et al: "Mass Variation Tests for Coating Tablets and Hard Capsules: Rational Application of Mass Variation Tests", Chemical and Pharmaceutical Bulletin, vol. 50, No. 9, Sep. 2002 pp. 1176-1180.

Anonymous: "Tablet coating ID—Chromatography Forum" , Apr. 17, 2012 (Apr. 17, 2012), XP055976221, Retrieved from the Internet: URL:https://chromforum.org/viewtopic.php?t=19631 [retrieved on Oct. 31, 2022].

European Search Report for European Patent Application No. 20788530.2 dated Nov. 9, 2022, 9 pages.

International Search Report for PCT/US2020/026990 mailed Jun. 26, 2020, 2 pages.

International Preliminary Report on Patentability for PCT/US2020/026990 mailed Oct. 21, 2021.

Kirchner et al: "Thin-layer chromatographic quantitative analysis", Journal of Chromatography A, Elsevier, Amsterdam, NL, vol. 82, No. 1, Aug. 1, 1973 (Aug. 1, 1973), pp. 101-115.

Office Action for European Patent Application No. 20 788 530.2 dated Nov. 28, 2023, 6 pages.

Kautsky, MP., "Steroid Analysis by HPLC", Recent Applications, Department of Obstetrics and Gynecology, University of Colorado School of Medicine, Denver, Colorado, Marcel Dekker, Inc. 1981, 4 pages.

Marie P. Kautsky, Steroid Analysis by HPLC: Recent Applications, vol. 16, (1981), pp. 221-225.

* cited by examiner

ANALYTICAL METHOD

CROSS-REFERENCE TO RELATED APPLICATIONS

The present application is a national stage entry under 35 U.S.C. § 371 of International Application No. PCT/US2020/026990, filed on Apr. 7, 2020, which claims priority to U.S. Provisional Patent Application No. 62/831,104, filed on Apr. 8, 2019. The contents of these applications are hereby incorporated by reference in their entirety.

FIELD OF THE INVENTION

The present invention relates generally to polymer quantification in a dosage form. More particularly, the present invention relates to methods, systems, and kits for determining the total amount of a polymer, e.g., a coating polymer, in a dosage form.

BACKGROUND OF THE INVENTION

Size exclusion chromatography and similar methods utilize a stationary phase to separate and identify molecules based on their corresponding molecular weight. When a sample contains constituents with a wide range of molecular weights, multiple size exclusion columns may be used to separate and identify all constituents and to quantify each constituent individually.

Conventional methods for quantifying each constituent in a sample may prove challenging when the sample includes polydispersed polymers or a plurality of constituents having overlapping molecular weights. Polydispersed polymers or the presence of additional constituents with overlapping molecular weights may generate one or more broad peak(s) with multiple apexes (some with and some without baseline separation). Such data may be difficult to accurately integrate and quantify.

One way of quantifying the total amount of polymer in a softgel capsule coating as well as the total amount of a coating in a softgel capsule may be a "before and after" approach with respect to capsule weight where the weight of the capsule after coating is compared to the weight of the capsule before coating. However, a freshly coated softgel capsule is a dynamic system where water is immediately allowed to evaporate, thereby altering the weight of the coated capsule. When multiple variables contribute to the capsule's weight variations (e.g., fresh coating and water evaporation), it may be challenging to determine accurately each variable's contribution.

There exists a need to accurately and reliably quantify the total amount of a selected constituent (e.g., a coating polymer) in a dosage form.

OBJECTS AND SUMMARY OF THE INVENTION

It is an object of certain embodiments of the present invention to accurately, reliably, and efficiently determine the total amount of a polymer in a dosage form.

It is another object of certain embodiments of the present invention to separate a selected polymer that is to be quantified from one or more other dosage form constituents that might present a hurdle in accurate quantification of the total amount of the selected polymer.

It is a further object of certain embodiments of the present invention to design a high pressure liquid chromatography (HPLC) method where a selected polydisperse polymer elution may be represented in a single peak.

The above objects of the present invention and others may be achieved by the present invention which in some embodiments is directed to a method for determining the total amount of polymer in a dosage form, a method for preparing a sample for quantifying the total amount of polymer in a dosage form, a system for quantifying the total amount of polymer in a dosage form, and/or a kit for quantifying the total amount of polymer in a dosage form.

In one embodiment, the method for determining the total amount of a polymer (e.g., a coating polymer) in a dosage form may comprise analyzing a sample that has been subject to separation of the polymer (e.g., coating polymer) from one or more other constituents in the dosage form, wherein the one or more other constituents of the dosage form have a molecular weight range that overlaps with a molecular weight range of the polymer (e.g., coating polymer).

In certain embodiments, the method for determining the total amount of a polymer (e.g., a coating polymer) in a dosage form may comprise preparing a sample and analyzing the sample. In such embodiments, preparing the sample may comprise separating the polymer (e.g., coating polymer) from one or more other constituents of the dosage form. The one or more other constituents of the dosage form may have a molecular weight range that overlaps with a molecular weight range of the polymer (e.g., coating polymer).

In certain embodiments, the method for preparing a sample for quantification of a total amount of a polymer (e.g., a coating polymer) in a dosage form may comprise separating the polymer from one or more other constituents in the dosage form. The one or more other constituents of the dosage form may have a molecular weight range that overlaps with a molecular weight range of the polymer (e.g., coating polymer).

In some embodiments, the system for quantifying the total amount of a polymer (e.g., a coating polymer) in a dosage form may comprise a dosage form, a diluent, and one or more analytical tools. The dosage form may comprise a coating polymer and one or more constituents. The diluent may be the kind that is capable to selectively dissolve the polymer to be quantified (e.g., coating polymer) but not the one or more other constituents. The one or more analytical tools may be the kind used to preparing a sample to have its total amount of polymer quantified and/or for analyzing a sample (e.g., a vial, a pipette, an HPLC machine, an ultra performance liquid chromatography (UPLC) machine, a gel permeation or size exclusion or filtration column, a sonicator, a processor, a computer, a display, a centrifuge, and so on). The one or more analytical tools in the system may be operatively coupled to each other so that the system (with or without an individual) may be used to perform any of the method steps disclosed herein automatically (in response to an algorithm) and/or manually (through an individual).

In some embodiments, the kit for quantifying the total amount of a polymer (e.g., a coating polymer) in a dosage form may comprise a diluent, one or more analytical tools, and instructions. The diluent may be the kind that is capable to selectively dissolve the polymer to be quantified (e.g., coating polymer) but not the one or more other constituents. The one or more analytical tools may be the kind used to preparing a sample to have its total amount of polymer quantified and/or for analyzing a sample (e.g., a vial, a pipette, an HPLC machine, a UPLC machine, a gel permeation or size exclusion or filtration column, a sonicator, a processor, a computer, a display, a centrifuge, and so on).

The instructions may provide guidance for preparing a sample to have its total amount of polymer (e.g., coating polymer) quantified and/or for analyzing the sample.

A wide variety of polymers may be quantified according to the methods, systems, and kits disclosed herein. In certain embodiments, the shell of a dosage form may be analyzed and a sample containing the coating polymer used in that shell may be prepared and analyzed to quantify the total amount of coating polymer in the shell. In other embodiments, the fill of a dosage form may be analyzed and a sample containing a selected polymer in the fill may be prepared and analyzed to quantify the total amount of polymer in the fill. In yet other embodiments, the dosage form in its entirety may be analyzed and a sample containing a certain polymer from the dosage form may be prepared and analyzed to quantify the total amount of that certain polymer in the dosage form. While reference herein may be to a certain polymer or to a selected polymer in a singular form, it should be understood that in certain embodiments more than one polymer may be quantified.

The dosage forms disclosed herein may be solid or liquid and may include, without limitations, tablets, capsules (e.g., softgel capsules), beads, caplets, pellets, granules, solutions, and so on.

Although the present disclosure is written with methods, systems, and kits directed to quantifying the total amount of a polymer in a dosage form, the same methods could also apply to formulations outside of the pharmaceutical art. For instance, the methods disclosed herein may be used for quantifying the total amount of a particular polymer in a lubricant composition, plastic formulation, personal care formulations, and so on.

Furthermore, although the present disclosure is written in a manner directed to quantifying a total amount of a polymer in a formulation (e.g., a dosage form), the same embodiments could also apply to quantification of a total amount of any constituent in a formulation that is difficult to quantify due the constituent of interest being polydisperse and/or due to the constituent of interest having a molecular weight range that overlaps with the molecular weight range of another constituent in the formulation.

BRIEF DESCRIPTION OF THE DRAWINGS

The above and other features of the present disclosure, their nature, and various advantages will become more apparent upon consideration of the following detailed description, taken in conjunction with the accompanying drawings, in which.

DEFINITIONS

Figure 1:
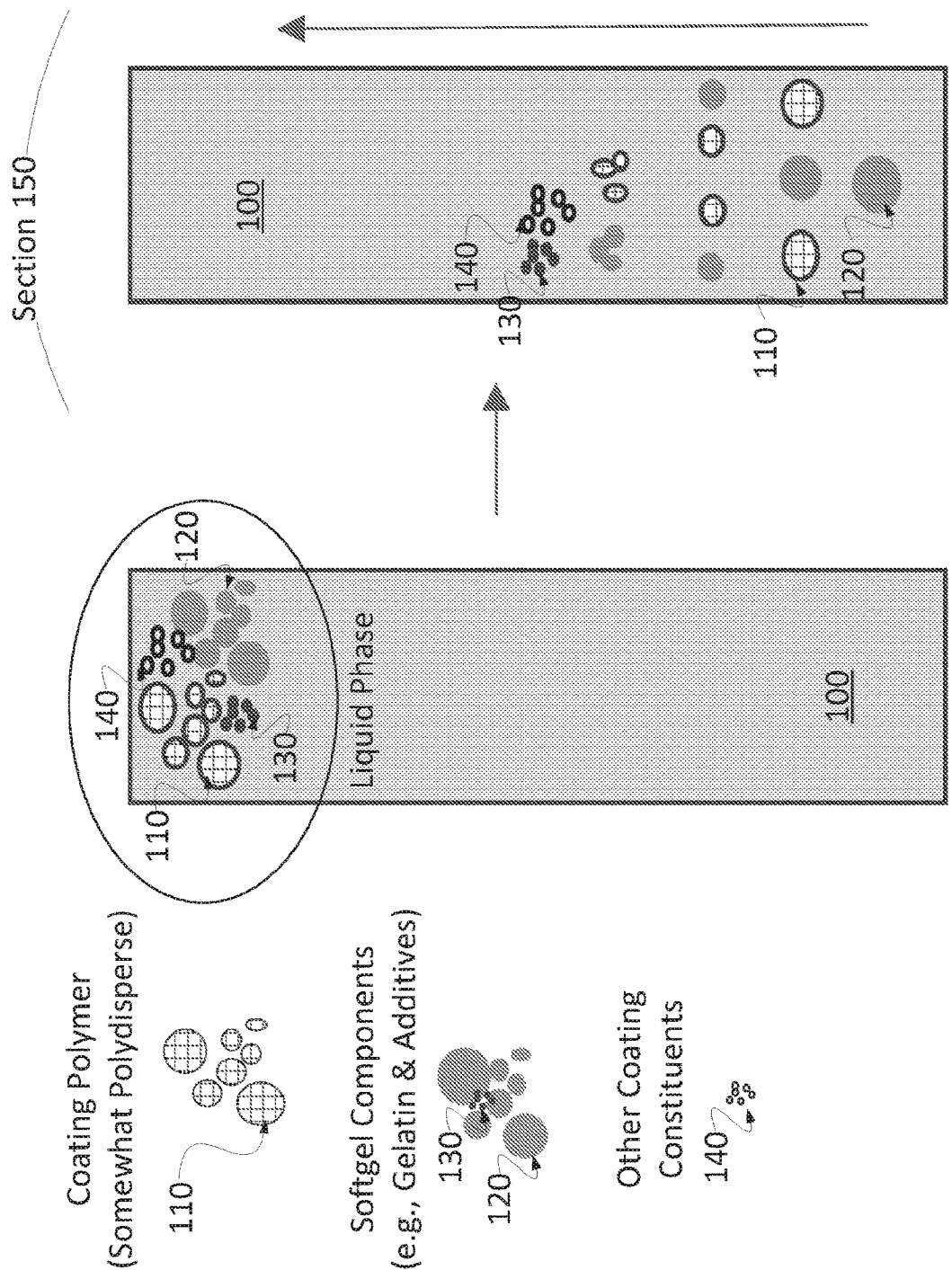
FIG. 1 illustrates dosage form constituent separation attained with a conventional gel permeation or size exclusion chromatography.

As used herein, the singular forms "a," "an," and "the" include plural references unless the context clearly indicates otherwise. Thus, for example, reference to "a polymer" includes a single polymer as well as a mixture of two or more identical or different polymers, and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number ±10%, such that "about 10" would include from 9 to 11.

As used herein, the terms "active agent," "active ingredient," "active pharmaceutical ingredient," "API," and "drug" refer to any material that is intended to produce a therapeutic, prophylactic, or other intended effect, whether or not approved by a government agency for that purpose. These terms with respect to specific agents include all pharmaceutically active agents, all pharmaceutically acceptable salts thereof, complexes, stereoisomers, crystalline forms, co-crystals, ether, esters, hydrates, solvates, and mixtures thereof, where the form is pharmaceutically active.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is nonsuperimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

"Pharmaceutically acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

The term "polydisperse" refers to molecules of varied sizes. For example, a "polydispersed polymer" refers to a polymer having a range of molecular weights.

The term "coating polymer" refers to a polymer used in a coating or a shell of a dosage form.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate certain materials and methods and does not pose a limitation on scope. No language in the specification should be construed as indicating any non-claimed element as essential to the practice of the disclosed materials and methods.

DETAILED DESCRIPTION

The present invention is directed to methods, systems, and kits for accurately, reliably, and efficiently determining the total amount of a polymer in a dosage form. The determination may occur by separating a selected polymer that is to be quantified from one or more dosage form constituents that may obstruct accurate quantification of the selected polymer.

The methods, systems, and kits disclosed herein may apply to a wide variety of polymers. In one embodiment, a coating polymer from a dosage form shell may be quantified as part of analysis of the dosage form shell by itself. In another embodiment, a fill polymer from a dosage form fill may be quantified as part of analysis of the dosage form fill by itself. In yet further embodiments, a selected polymer present in the dosage form (as a whole) may be quantified as part of analysis of the whole dosage form.

Some embodiments of the present disclosure may be implemented with analytical tools that are readily available, such as a high pressure liquid chromatography machine (HPLC), gel permeation column, size exclusion column, filtration column, sonicator, centrifuge, combinations thereof, and so on.

The difference between existing methods and the inventive methods disclosed herein may be better understood in light of the below description with respect to the figures. The description of the figures should be viewed as merely exemplary and non-limiting.

FIG. 1 illustrates dosage form constituent separation attained with a conventional gel permeation or size exclusion chromatography method. FIG. 1 depicts an attempt to quantify a coating polymer 110 in a shell of a dosage form (e.g., a softgel capsule). The shell of the exemplary softgel capsule may further comprise softgel components (e.g., gelatin 120 and additives 130) and one or more other coating constituents 140.

Existing analytical methods may utilize a gel permeation column or a size exclusion column 100 with a stationary phase to separate and identify polymers/molecules (e.g., the coating constituents) based on their corresponding molecular weight. Based on this principle, as shown in FIG. 1, section 150, large molecules (i.e., coating constituents with larger molecular weight) may elute first and smaller molecules (i.e., coating constituents with smaller molecular weight) may elute successively.

Since coating polymer 110 may be polydisperse, a plurality of gel permeation columns or size exclusion columns may be necessary to accurately and reliably separate, identify, and quantify the polydisperse coating polymer and the one or more other constituents in a sample that is being analyzed. A polydisperse polymer may also elute over a long duration and appear on a chromatogram as a very broad peak with multiple apexes, or as a plurality of peaks (some with and some without baseline separation). Such chromatograms may be challenging to integrate lending to difficulty in accurately quantifying the coating polymer.

Furthermore, coating polymer 110 and gelatin 120 may co-elute since gelatin 120 may also be polydisperse and may have overlapping molecular weight range with the molecular weight range of coating polymer 110. Thus, the gelatin may interfere with accurate quantification of the coating polymer.

The inventive methods disclosed herein use a combination of sample preparation and column selection to: 1) remove one or more dosage form constituents that may present a hurdle in accurate quantification of the amount of coating polymer (e.g., coating polymer); and 2) elute the polymer in a manner that is easier to quantify.

Figure 2:
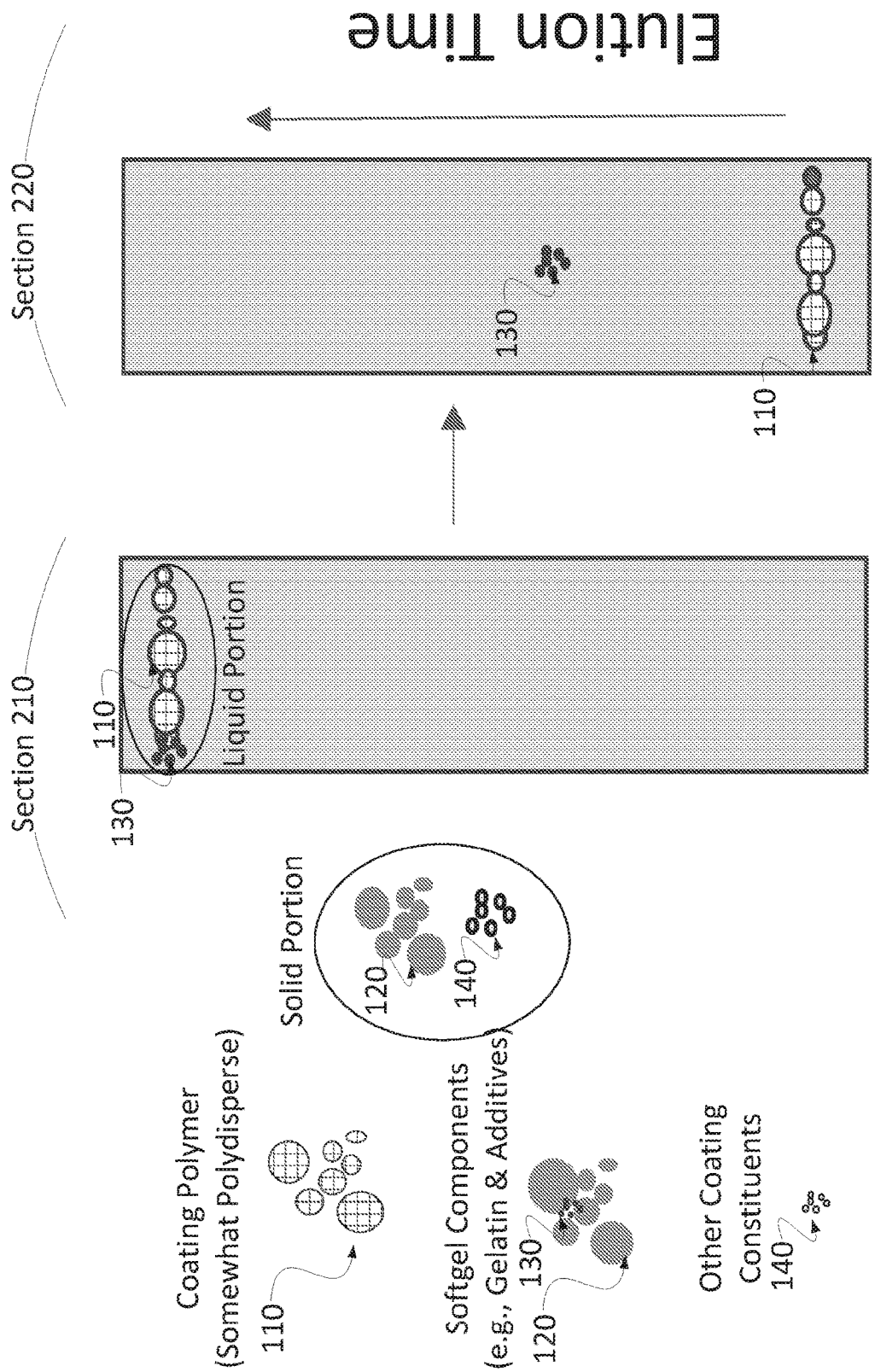
FIG. 2 illustrates dosage form constituent separation attained with a method according to embodiments disclosed herein.

FIG. 2 illustrates dosage form constituent separation attained with a method according to embodiments disclosed herein. In the example depicted in FIGS. 1 and 2, the molecular weight range of gelatin 120 overlaps with the molecular weight range of at least some of coating polymer 110. The methods disclosed herein may take the approach of separating a polymer that it to be quantified from one or more other dosage form constituents that have a molecular weight range that overlaps with the molecular weight range of the polymer to be quantified.

In certain embodiments, the methods disclosed comprise preparing a sample (for quantification of the total amount of polymer in the sample) by separating the coating polymer from one or more constituents that may interfere with accurate quantification of the coating polymer (e.g., gelatin). Separating the coating polymer from one or more constituents in the dosage form may comprise mixing the dosage form with a diluent to selectively dissolve the coating polymer in the diluent. The phrase "diluent to selectively dissolve" as used herein refers to a particular solvent (e.g., dimethylformamide (DMF)) chosen due to its ability to dissolve the component/analyte of interest (e.g., a coating polymer) without dissolving a component that could interfere (e.g., gelatin, carrageenan, starch, pectin, combinations thereof, and so on) with the quantification of component/analyte of interest if both were dissolved. Exemplary diluents that may be used include, without limitations, one or more of acetone, acetonitrile, benzene, carbon tetrachloride, chlorobenzene, chloroform, cyclohexane, dichloroethane, diethyl ether, dimethylformamide, 1,4-dioxane, ethyl acetate, 100% ethanol, methanol, methylene chloride, methyl t-butyl ether, nitromethane, pentane, petroleum ether, tetrahydrofuran, toluene, o-xylene, m-xylene, p-xylene.

In certain embodiments, once the dosage form is mixed with a diluent that selectively dissolves the coating polymer but not one or more other constituents, additional steps may be taken to separate the dissolved coating polymer from the one or more insoluble other constituents. For example, the dosage form in diluent may be sonicated and/or centrifuged and/or subjected to other steps to separate the liquid portion from the solid portion (as shown in FIG. 2, section 210). The liquid portion would form a sample that may be further analyzed to quantify the total amount of polymer.

Analyzing the sample may comprise running it through a size exclusion column or through a gel permeation column or through a filtration column to further separate the polymer of interest (e.g., coating polymer) from other components that were dissolved in the selective diluent (as shown in FIG. 2, section 220).

If the sample is run through a gel permeation column or a size exclusion column or a filtration column, the molecular weight range of the polymer of interest should be considered when selecting a column. Specifically, the column's rated range of separation (with regard to the molecular weight) should be lower than the lower end of the polymer's molecular weight range. For example, if the polydispersed polymer's molecular weight ranges from about 55 kDa to about 75 kDa (also may be referred to herein as a "first range of molecular weight"), the column's maximum molecular weight separation should be under about 55 kDa (also may be referred to herein as a "second range of molecular weight"). In the methods disclosed herein, the first range of molecular weight (i.e., of the polydispersed polymer of interest) may be greater than the second range of molecular weight (i.e., of the column). Such column selection would result in the polydispersed polymer eluting in a single peak at the beginning of an HPLC run. Essentially, the entire range of molecular weights of the polydisperse polymer may be combined in a single peak that may be used to quantify the total amount of polymer.

Analyzing the sample may further comprise quantifying the total amount of a polymer of interest in a dosage form, in a shell, in a coating, in a fill, or in a sample. When the sample is run through an HPLC size exclusion or gel permeation or filtration column, the quantification may be done through a chromatogram (e.g., by integrating a peak in the chromatogram).

In some embodiments, the method steps disclosed herein may be performed by one person, by several individuals, or may be automated and performed on one or more analytical tools. For example, in one embodiment, preparing a sample may be performed by one or more individual(s) utilizing one or more analytical tool(s) (e.g., sonicator and centrifuge), analyzing the sample may be performed partially in one or more analytical tool(s) (e.g., HPLC/UPLC machine and size exclusion/gel permeation/filtration column) and partially by one or more individual(s) or by a processor configured to quantify an amount of an eluted component (e.g., by integrating a chromatogram peak that corresponds to said eluted component).

The advantages of the methods disclosed herein include, but are not limited to: 1) accurate and reliable quantification of a selected dosage form constituent (e.g., a coating polymer) based on a single elution peak; 2) quicker results since the polymer of interest elutes as part of the excluded volume, which elutes first in an HPLC run; 3) elimination of specificity concerns by separating (e.g., through selective dissolution) a selected dosage form constituent (e.g., a coating polymer) from one or more other dosage form constituents (e.g., gelatin and/or carrageenan) that may interfere with quantifying the total amount of the selected dosage form constituent; 4) ability to accurately and reliably measure the total amount of a selected dosage form constituent at various stages of the dosage form preparation (e.g., during a curing step of a capsule coating process); 5) potential to become a validation method due to its ability to yield consistent measurements repeatedly; and 6) scalable up to a commercial scale.

In some embodiments, this disclosure may be directed to a system for quantifying the total amount of a selected dosage form constituent (e.g., a coating polymer). The system may comprise a dosage form (e.g., one that comprises a coating polymer and one or more other constituents), a diluent (e.g., the kind capable of selectively dissolving the selected dosage form constituent but not one or more of the other dosage form constituents), and one or more analytical tools (e.g., the kind that may be used for preparing or for analyzing a sample with respect to its total amount of a selected dosage form constituent).

Exemplary analytical tools that may be part of the systems disclosed herein include, without limitations, an HPLC machine, a UPLC machine, a size exclusion column, a gel permeation column, a filtration column, a sonicator, a centrifuge, a processor, a computer, a display, and any combination thereof. Any combination of analytical tools that may form the systems disclosed herein may be operatively connected. In certain embodiments, the one or more analytical tool(s) may be separate and an individual may manually utilize various analytical tools in the order they see fit to implement methods disclosed herein. In other embodiments, the one or more analytical tool(s) may be operatively connected such that methods for quantifying the total amount of a particular dosage form constituent may be automated and may perform the method in response to a programmed algorithm.

In some embodiments, this disclosure may be directed to a kit for quantifying the total amount of a selected dosage form constituent (e.g., a coating polymer). The kit may comprise a diluent (e.g., the kind capable of selectively dissolving the selected dosage form constituent but not one or more of the other dosage form constituents), one or more analytical tools (e.g., the kind that may be used for preparing or for analyzing a sample with respect to its total amount of a selected dosage form constituent), and instructions for preparing a sample to have its total amount of a selected dosage form constituent quantified and/or for analyzing the sample.

In some embodiments, the kit may be customized depending on the selected dosage form constituent to be quantified. For instance, a suitable diluent and/or a suitable size exclusion/gel permeation/filtration column may be included in the kit.

The dosage forms that may be analyzed with the methods, systems, and kits disclosed herein may be solid or liquid. In some embodiments, the dosage forms may be selected from the group consisting of tablets, capsules, beads, caplets, pellets, granules, solutions and combinations thereof. In one embodiment, the dosage form may be a tablet or a capsule. In one embodiment, the dosage form may be a softgel capsule or an optishell capsule. Solid dosage forms disclosed herein may have different shapes (e.g., round, oval, oblong, spherical, or a non-standard shape) and sizes.

The dosage forms disclosed herein comprise a shell and/or may be coated with one or more coatings, including but not limited to, immediate release coatings, protective coatings, enteric or delayed release coatings, sustained release coatings, barrier coatings, moisture shield coatings and combinations thereof. The one or more coatings on the dosage forms may be useful to provide controlled release of an active ingredient from the dosage form, protect the dosage form from interactions with other components, or deliver one or more active ingredients from the dosage form at a particular release profile.

The shell of capsules (e.g., of soft gelatin capsule) may be formed from plasticized gelatin, carrageenan, starch, pectin, or other functional polymeric materials (e.g., polysaccharides (e.g., pullulan, alteman, dextrans, starches), polyvinyl alcohol, chitosan, polylactic acid, poly(lactic-co-glycolic acid), alginate, gum arabic, guar gum, whey protein, soy protein, zein, casein, combinations thereof, functionalized and co-polymers thereof) that are typically used for encapsulation of liquids, fluids, pastes or other fill materials.

The liquid fill or semi-solid fill of a capsule dosage form (if present) may comprise one or more liquids or semi-solids that are compatible with the capsule shell. The liquid fill or semi-solid fill may comprise one or more combinations of fluids that may be broadly categorized as hydrophilic or lipophilic.

A lipophilic liquid fill or semi-solid fill may be an oil form of an active ingredient, an active ingredient or multiple active ingredient preparations that may be solutions, suspensions, emulsions, micro-emulsions, self-emulsifying systems, gels, and other liquids or semi-solids that will be known to those who are expert in the field of capsule formulations.

Examples of useful oils include omega-3 fatty acids triglycerides (e.g., alpha-linolenic acid, eicosapentaenoic acid and docosahexaenoic acid), ethyl esters, vegetable oils, mineral oils or other food grade oil. Vegetable oils may include castor bean oil, coconut oil, peanut oil, palm kernel oil, canola oil, avocado oil, evening primrose oil, rice bran oil, borage oil, sunflower oil, soybean oil, palm oil, corn oil and safflower oil.

Hydrophilic liquid fill or semi-solid fill are typically based on polyethylene glycols commonly referred to as PEG and may include lesser amounts of glycerol, propylene glycol and water. Other hydrophilic materials used to a lesser extent include, but not limited to, methoxypolyethylene glycols, diethyleneglycol monoethyl ether tetrahyrofurfuryl alcohol polyethylene glycol, propylene carbonate, n-methyl-2-pyrrolidone, polyoxyethylene-poly-oxypropylene copolymers benzyl alcohol and ethyl alcohol.

The fill materials may also include excipients known in the art of capsule encapsulation such as dispersants, surfactants, plasticizers, flavoring agents, opacifying agents, preservatives, embrittlement inhibiting agents, colorants, dyes and pigments, and disintegrants.

Typical immediate release coating films that may be used on the shell of a capsule are hydro-alcoholic film coatings or cellulose film coating systems as used in various pharmaceutical solid oral dosage forms. Typical coating systems may be aqueous, alcohol or organic solvent based or combinations containing hydroxy-propyl-methyl cellulose and derivatives, and polyvinyl alcohol and derivatives.

Examples of film coated dosage forms (e.g., tablets, beads, capsules) that could be used as the solid inclusions to be encapsulated include, without limitations, Amoxicillin, Azithromycin, Atenolol, Amlodipine, Acelofenac, Amtriptyline, Ampicillin HCl, Ciprofloxacin, Cefadroxil HCl, Celecoxib, Cimitidine, Calcium Tablets, Certizine HCl, Clarithromycin, Chloroquine Phosphate, Erythromycin estolate, Erythromycin striate, Enalpril Maleate, Elctronxib, Ferrous, fumarate, Famotidine, Flupenthixol, Fluoxetine Felodipine, Gatifloxacin, Gliclazide, Ibuprofen, lndapamide, Ketorolac, Ketoprofen, Levofixation, Levocetrinzie, Losartan, Potassium, Levamisole, Metormin, Methylopa, Metra+Tetraozole, Metronidozole, Methyl, Comblamine, Mefenamic acid, Metropralal Nifedipne, Norfloxacin, Nifedopine, Norfloxacin, Norflax+Tindazole, Oflaxacin, Oflaxacin+Omidazole, Olazzapine, Orridazole, Oflexacin+Omidazole Paracetamol, Pravastain, Prmethazine, Quinine, sulphate, Primaquine, Ramipril, Tindazole, Tiri+Doxicycline, Tiri+Tetracyline, Valdecoxib, Verapamil, herbal and Neutraceuticals.

Typical protective coatings that may be used on the shell of a capsule may include, but are not limited to, polymer, antioxidants, chelating agents, colours or dyes.

Typical enteric coatings that may be used on the shell of a capsule comprise, but are not limited to, one or more of the following recognized coating agents: methyl acrylate-methacrylic acid copolymers, methacrylic acid-ethyl acrylate copolymer (e.g., Kollicoat® MAE 30 D, EUDRAGIT® L 30 D), cellulose acetate succinate, hydroxy propyl methyl cellulose phthalate, hydroxy propyl methyl cellulose acetate succinate (hypromellose acetate succinate), polyvinyl acetate (optionally stabilized with polyvinylpyrrolidone and sodium lauryl sulfate, such as Kollicoat® SR 30 D), polyvinyl acetate phthalate (PVAP), methyl methacrylate-methacrylic acid copolymers, sodium alginate/alginic acid and stearic acid, ammonium methacrylate copolymer (e.g., EUDRAGIT® RS 30 D, EUDRAGIT® RL 30 D), acrylate copolymers (e.g., EUDRAGIT® NE 30 D).

Examples of enteric coated dosage forms (e.g., tablets, beads, capsules) include: Aspirin and Clopidogrel combination, Aspirin, Bisacodyl, Diclofenac-sodium, Doxylamine succinate, Esomeprazole, Garlic Tablets, Lansoprazole, Omeparazole, Pantoprazole, Pentoxyfilline, Pancreatin, Rabeprazole, Serratiopeptidase, and Sodium Valproate.

Sustained release capsules may be film coated, enteric coated, or polymer matrix formulated. Sustained release film coatings may include, but are not limited to, a water insoluble material such as a wax or wax-like substance, fatty alcohols, shellac, zein, hydrogenated vegetable oils, water insoluble celluloses, polymers of acrylic and/or methacrylic acid, and any other slowly digestible or dispersible solids known in the art.

Examples of sustained release dosage forms include, without limitations: Acetazolamide Pellets, Aminophylline, Amitriptyline Pellets, Captoprill, Diclofenac Sodium, Diltiazem, Gliclazide, Iron, Levodopa, Lithium Carbonate, Metformin, Methyldopa, Nifedipine, Salbutamol Sulphate, Theophylline, Verapamil HCL, vitamin supplements, mineral supplements, and vitamins with Zinc.

Moisture shield coatings provide moisture barriers for moisture sensitive or hygroscopic drugs. Such coatings may be applied to a capsule to protect the capsule form moisture resulting from, for example, the encapsulation process (if it utilizes water as a processing aid).

Examples of dosage forms incorporating moisture shield coatings include, but are not limited to: Amitriyptyline HCl, Amoxycillin and Clavulanic Acid combination, Atorvastatin and Calcium combination, Calcium Tablets, Clopidogrel, Ethambutol, Glucosamine and Chondritin combination, certain Herbal products, Multivitamins, Proton Pump Inhibitors Ranitidine HCl, Rifampicin and other moisture sensitive drugs.

The present invention contemplates the use of any active ingredients known in the art. It is well within the knowledge of a skilled person in the art to select a particular combination of active ingredients or medicaments. In some embodiments, active ingredients may include, but are not limited to, the following: APIs, nutraceuticals, nutritional supplements, therapeutic substances, and functional excipients.

Suitable APIs may include, but are not limited to, the following: analgesics, anti-inflammatory agents, anti-helminthics, anti-arrhythmic agents, anti-asthma agents, antibacterial agents, anti-viral agents, anti-coagulants, anti-dementia agents, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, immunosuppressants, anti-protozoal agents, anti-pyretics anti-thyroid agents, anti-tussives, anxiolytics, sedatives, hypnotics, neuroleptics, neuroprotective agents, beta-blockers, cardiac inotropic agents, cell adhesion inhibitors, corticosteroids, cytokine receptor activity modulators, diuretics, anti-Parkinson's agents, gastrointestinal agents, histamine H-receptor antagonists, HMG-CoA reductase inhibitors, keratolytics, lipid regulating agents, muscle relaxants, nitrates and other anti-anginal agents, non-steroid anti-asthma agents, nutritional agents, opioid analgesics, sex hormones, stimulants, and anti-erectile dysfunction agents.

Suitable nutraceuticals may include, but are not limited to, 5-hydroxytryptophan, acetyl L-carnitine, alpha lipoic acid, alpha-ketoglutarates, bee products, betaine hydrochloride, bovine cartilage, caffeine, cetyl myristoleate, charcoal, chitosan, choline, chondroitin sulfate, coenzyme Q10, collagen, colostrum, creatine, cyanocobalamin (Vitamin 812), dimethylaminoethanol, fumaric acid, germanium sequioxide, glandular products, glucosamine HCl, glucosamine sulfate, hydroxyl methyl butyrate, immunoglobulin, lactic acid, L-Carnitine, liver products, malic acid, maltose-anhydrous, mannose (d-mannose), methyl sulfonyl methane, phytosterols, picolinic acid, pyruvate, red yeast extract, S-adenosylmethionine, selenium yeast, shark cartilage, theobromine, vanadyl sulfate, and yeast.

Suitable nutritional supplements may include vitamins, minerals, fiber, fatty acids, amino acids, herbal supplements or a combination thereof.

Suitable vitamins may include, but are not limited to, the following: ascorbic acid (Vitamin C), B vitamins, biotin, fat soluble vitamins, folic acid, hydroxycitric acid, inositol, mineral ascorbates, mixed tocopherols, niacin (Vitamin B3), orotic acid, para-aminobenzoic acid, panthothenates, panthothenic acid (Vitamin B5), pyridoxine hydrochloride (Vitamin B6), riboflavin (Vitamin B2), synthetic vitamins, thiamine (Vitamin B1), tocotrienols, vitamin A, vitamin D, vitamin E, vitamin F, vitamin K, vitamin oils and oil soluble vitamins.

Suitable herbal supplements may include, but are not limited to, the following: arnica, bilberry, black cohosh, cat's claw, chamomile, echinacea, evening primrose oil, fenugreek, flaxseed, feverfew, garlic, ginger root, ginko biloba, ginseng, goldenrod, hawthorn, kava-kava, licorice, milk thistle, psyllium, rauowolfia, senna, soybean, St. John's wort, saw palmetto, turmeric, valerian. Minerals may include, but are not limited to, the following: boron, calcium, chelated minerals, chloride, chromium, coated minerals, cobalt, copper, dolomite, iodine, iron, magnesium, manganese, mineral premixes, mineral products, molybdenum, phosphorus, potassium, selenium, sodium, vanadium, malic acid, pyruvate, zinc and other minerals.

ILLUSTRATIVE EXAMPLES

The following examples are set forth to assist in understanding the invention and should not, of course, be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

Example 1

TABLE 1

Exemplary Implementation of a Method According to an Embodiment

| | Inventive Method |
|---|---|
| Instrument Type | HPLC |
| Detector | Refractive Index |
| Detector Temperature | 40° C. |
| Column(s) | Polymer Dependent: any non-mixed bed column where the molecular weight range of the desired analyte is excluded from the column without separation. In the case of Eudragit NE 30 a Phenomenex Phenogel 10e4 Å, 10 μ, 7.8 × 300 mm was used. |
| Column Temperature | 40° C. |
| Mobile Phase/Diluent | Dimethylformamide (DMF) |
| Injection Volume | 100 μL |
| Runtime | 15 minutes |
| Sample Preparation | Into a 200 mL clear volumetric flask, add 10 softgel capsules. Pipet 100.0 mL of diluent into the flask and cap. Place in sonication bath for 30 minutes. Gently swirl the flask and sonicate for another 15 minutes. Gently swirl the flask and sonicate for an additional 15 minutes. Invert flask 20 times, remove ~5 mL and centrifuge. Add the supernate to an HPLC vial. |

Table 1 depicts an exemplary implementation of a method according to embodiments disclosed herein for quantifying the total amount of a coating polymer in the shell of a softgel capsule. The method utilizes an HPLC machine and a refractive index detector at 40° C.

In this example, the polymer that was quantified was Eudragit® NE 30D with a molecular weight of about 700 kDa.

While conventional methods may use a plurality of size exclusion or gel permeation columns, the inventive method exemplified herein uses a single non-mixed bed column where the molecular weight range of the Eudragit® NE 30D is excluded from the column without separation (Phenomenex Phenogel 10e4 Å, 10μ, 7.8×300 mm). The selected column in the inventive method has a molecular weight cut-off of about 500 kDa. Therefore, any polymer with a molecular weight greater than 500 kDa (such as Eudragit® NE 30D with a molecular weight of 700 kDa) would not retain on the column and would elute quickly (as depicted in the first chromatogram peak) without separation.

The diluent used in the exemplified inventive method to selectively dissolve the Eudragit® NE 30D polymer and not the gelatin was dimethylformamide (DMF).

Once the proper column and diluent is selected for the exemplified inventive method, sample preparation may begin. The dosage form (e.g., softgel capsule) may be stirred with the selected diluent (e.g, DMF) until the polymer in the coating (e.g., Eudragit® NE 30D) is freely dissolved in the solvent but the other softgel capsule constituents (e.g., gelatin) are not. The dosage form in solvent may be further processed as described in the table (e.g., sonicating, swirling, inverting, centrifuging, etc) to arrive at a final sample. The final sample may be injected into an HPLC instrument to analyze and quantify the selected dosage form constituent. The parameters of the HPLC method (e.g., flow rate, mobile phase, column temperature, detector temperature, etc) may be altered and optimized to arrive at an optimal chromatogram peak shape.

The total amount of a selected dosage form constituent (coating polymer) as well as the total amount of coating on a softgel capsule may be calculated from the resulting chromatograms.

Example 2

TABLE 2

Exemplary Implementation of a Method According to an Embodiment

| | Inventive Method |
|---|---|
| Instrument Type | HPLC |
| Detector | Refractive Index |
| Detector Temperature | 40° C. |
| Column(s) | Polymer Dependent: any non-mixed bed column where the molecular weight range of the desired analyte is excluded from the column without separation. In the case of Kollicoat SR30D a Phenogel 5 μm 100 Å, LC Column 300 × 4.6 mm was used. |
| Column Temperature | 40° C. |
| Mobile Phase/Diluent | Dimethylformamide (DMF) |
| Injection Volume | 100 μL |

TABLE 2-continued

Exemplary Implementation of a Method According to an Embodiment

Inventive Method

| | |
|---|---|
| Runtime | 15 minutes at a flow rate of 1.0 mL/min |
| Sample Preparation | Standard Preparation: Kollicoat SR30D was added directly to a 10 mL volumetric flask and brought to volume with DMF diluent. The concentration of polymer was determined using the manufacturer Certificate of Analysis. Sample Preparation Softgel capsules were stirred into 100 mL of DMF diluent until the coating was completely dissolved as assessed visually after approximately two hours. The sample was added to an HPLC vial and analyzed via HPLC. |

Table 2 depicts an exemplary implementation of a method according to embodiments disclosed herein for quantifying the total amount of a coating polymer in the shell of a softgel capsule. The method utilizes an HPLC machine and a refractive index detector at 40° C.

In this example, the polymer that was quantified was Kollicoat® SR30D that coated softgel ibuprofen capsules.

The standard used in this example was a Kollicoat SR30D sample that was added directly to a volumetric flask and brought to volume with a diluent (DMF).

Figure 3:
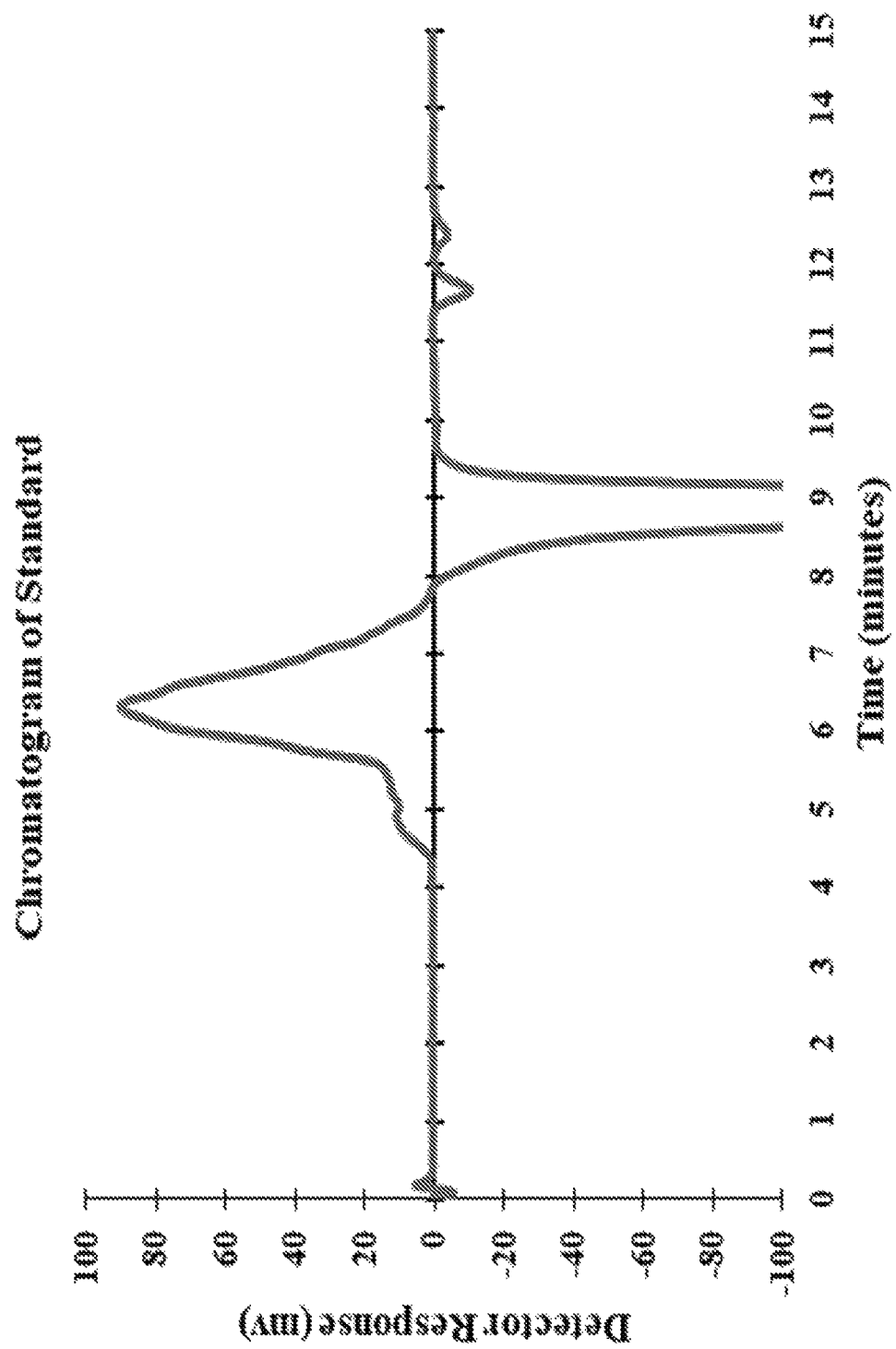
FIG. 3 illustrates an exemplary chromatogram of a standard.
Figure 4:
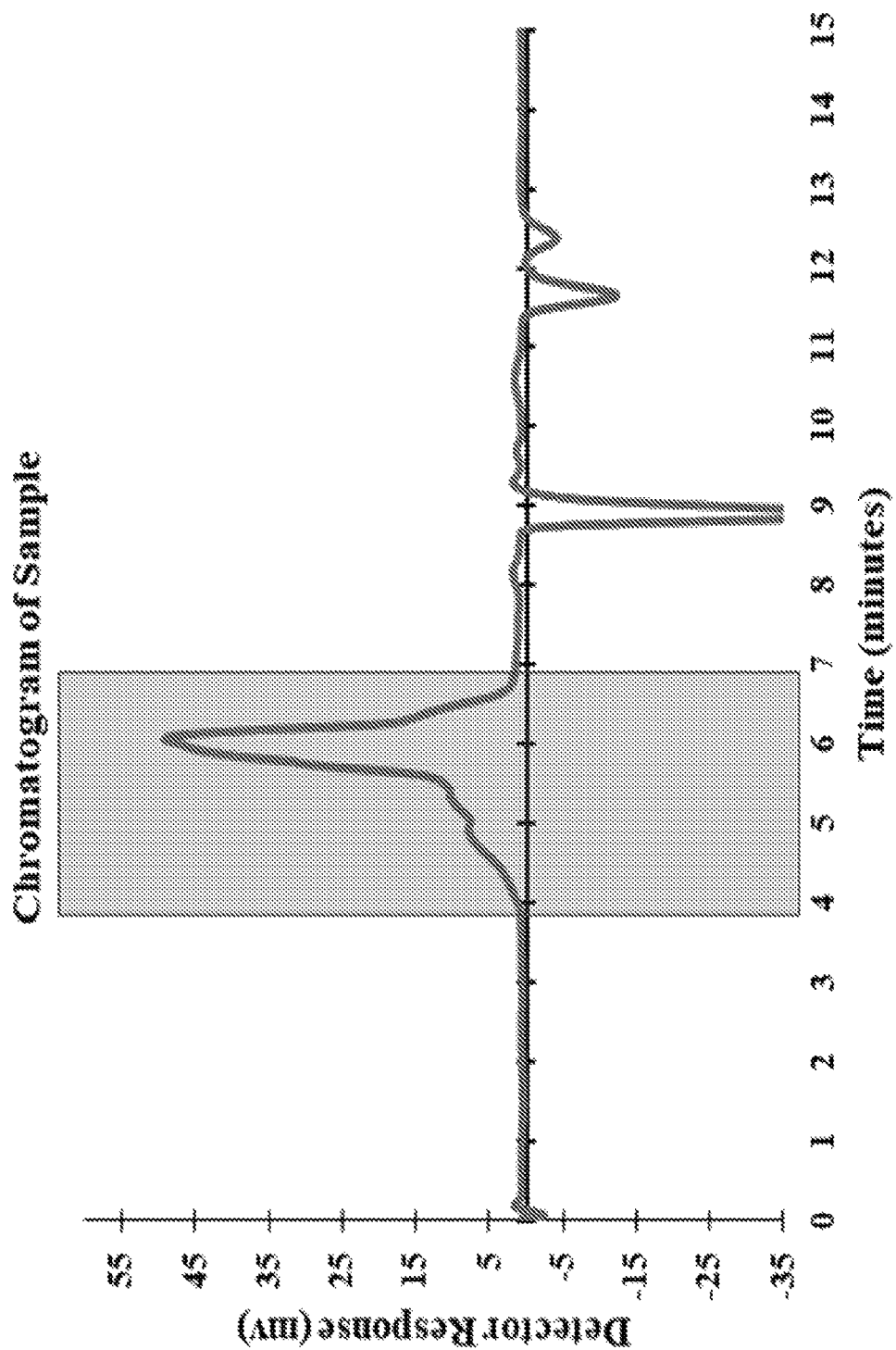
FIG. 4 illustrates an exemplary chromatogram of a sample analyzed according to embodiments disclosed herein.

While conventional methods may use a plurality of size exclusion or gel permeation columns, the inventive method exemplified herein uses a single non-mixed bed column where the molecular weight range of the Kollicoat SR30D is excluded from the column without separation. The selected column in the inventive method has a molecular weight cut-off such that Kollicoat SR30D would not retain on the column and would elute quickly without separation, as depicted in the first chromatogram peak of the standard in FIG. 3 and in the first chromatogram peak of the softgel samples in FIG. 4.

The diluent used in the exemplified inventive method to selectively dissolve the Kollicoat SR30D polymer was dimethylformamide (DMF).

Once the proper column and diluent is selected for the exemplified inventive method, sample preparation may begin. The dosage form (e.g., softgel capsule) may be stirred with the selected diluent (e.g, DMF) until the polymer in the coating (e.g., Kollicoat SR30D) is freely dissolved in the solvent but the other softgel capsule constituents (e.g., gelatin) are not. The final sample may be injected into an HPLC instrument to analyze and quantify the selected dosage form constituent. The parameters of the HPLC method (e.g., flow rate, mobile phase, column temperature, detector temperature, etc) may be altered and optimized to arrive at an optimal chromatogram peak shape.

The total amount of a selected dosage form constituent (coating polymer) as well as the total amount of coating on a softgel capsule may be calculated from the resulting chromatograms. Table 3 below depicts the total amount of coating polymer (Kollicoat SR30D) in the softgel samples that were analyzed using the method described herein.

TABLE 3

Results

| | |
|---|---|
| Percent Relative Standard Deviation of All Working Standards | 1.4% |
| Number of Softgels in Sample Preparation | 5 Softgels |
| Amount of Coating on Softgels (Theoretical) | 119.00 mg |

TABLE 3-continued

Results

| | |
|---|---|
| Amount of Coating on Softgels (Experimental) | 116.62 mg |
| Percent of Theoretical Amount of Coating Detected by Method described herein | 98% |

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. A method of determining a total amount of a coating polymer in a dosage form, the method comprising:
   preparing a sample by separating the coating polymer from one or more other constituents of the dosage form, wherein the coating polymer comprises polydispersed polymers, and
   analyzing the sample,
   wherein the one or more other constituents of the dosage form have a molecular weight that overlaps with a molecular weight range of the coating polymer.

2. The method of claim 1, wherein separating comprises mixing the dosage form with a diluent to selectively dissolve the coating polymer in the diluent.

3. The method of claim 2, wherein the diluent is capable of dissolving the coating polymer but not the one or more other constituents of the dosage form.

4. The method of claim 2, wherein the diluent is dimethylformamide (DMF).

5. The method of claim 2, wherein separating further comprises sonicating a mixture of the dosage form in the diluent.

6. The method of claim 2, wherein separating further comprises centrifuging a mixture of the dosage form in the diluent.

7. The method of claim 2, wherein the dosage form is a tablet or a capsule.

8. The method of claim 7, wherein the dosage form is a softgel capsule.

9. The method of claim 1, wherein the one or more other constituents of the dosage form comprise gelatin, carrageenan, starch, pectin, or combinations thereof.

10. The method of claim 1, wherein analyzing the sample comprises running the sample through a size exclusion, a gel permeation, or a filtration column.

11. The method of claim 10, wherein the coating polymer in the dosage form have a first range of molecular weight, wherein the size exclusion, the gel permeation, or the filtration column have a range of separation that corresponds to a second range of molecular weight, and wherein the first range of molecular weight is greater than the second range of molecular weight.

12. A method of preparing a sample for quantification of a total amount of a coating polymer in a dosage form, the method comprising:
   separating a coating polymer from one or more other constituents in a dosage form, wherein the coating polymer comprises polydispersed polymers,
   wherein the one or more other constituents of the dosage form have a molecular weight that overlaps with a molecular weight range of the coating polymer.

* * * * *